June 13, 1967 J. M. GARABEDIAN Plant Pat. 2,747
PLUM TREE
Filed May 2, 1966
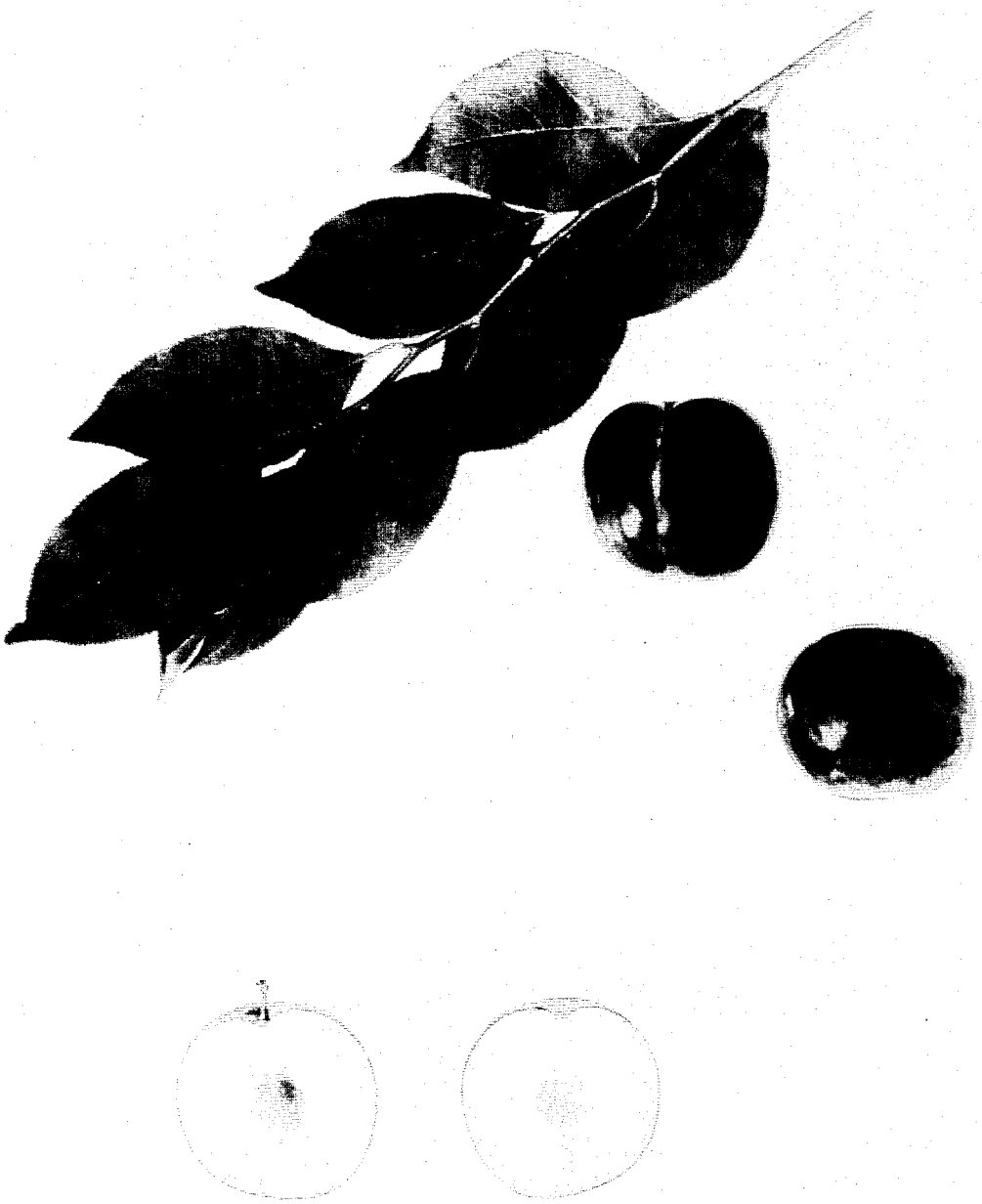
INVENTOR
John M. Garabedian
BY
Webster & Webster
ATTORNEYS United States Patent Office Plant Pat. 2,747

Patented June 13, 1967

2,747

PLUM TREE

John M. Garabedian, Fresno, Calif., assignor to Peach & Willow Farms, Fresno, Calif., a corporation of California Filed May 2, 1966, Ser. No. 547,136
1 Claim. (Cl. Plt.—38)

The present invention relates to a new and distinct variety of plum tree which bears commercially desirable fruit having yellowish amber flesh, a free to semi-free stone, and deep purple blue skin.

In comparison with the Queen Ann (unpatented), the fruit of the present variety of plum tree—while similar in the color of the skin—is characteristically novel by virtue of a ripening period about four to five weeks later and which beneficially extends the fresh fruit season for the instant type of plum.

The fruit of the present variety, in further comparison with the Queen Ann, has firmer flesh which does not soften as readily; the shelf life of the fruit thus being longer.

Additionally, the fruit of the present variety is slightly smaller than the Queen Ann and is roundish-oblate in form instead of oblong.

The present variety of plum tree was originated by me, as an open pollinated seedling of Queen Ann, in the following manner:

Seeds of the Queen Ann, gathered by me from my orchard in Madera County, Calif., were professionally germinated in flats for my account. The resulting seedlings were planted in a nursery plot on my ranch in Fresno County, Calif. Of these seedlings, one evidenced special promise as a commercial variety and was selected by me for asexual reproduction; such selection being the present variety.

Asexual reproduction of such variety was accomplished by me in an orchard on my ranch in Fresno County, Calif., by budding on mature nectarine trees; such reproductions having run true to the original tree in all respects.

The drawing comprises an illustration, by photographic reproduction in color, of a twig with leaves; two of the whole fruit; and one fruit cut in half to expose the flesh and with the stone remaining in place in one half.

Referring now more specifically to the pomological details of this new and distinct variety of plum tree, the following is an outline description thereof; all major color plate identifications, by comparison with fresh specimens, being by reference to Maerz and Paul Dictionary of Color, except where common terms of color definition are employed.

Tree:
- *Size.*—Medium.
- *Vigor.*—Medium.
- *Growth.*—Spreading.
- *Density.*—Open.
- *Form.*—Vase shaped.
- *Hardiness.*—Hardy.
- *Production.*—Productive.
- *Bearing.*—Regular bearer.

Trunk:
- *Form.*—Medium.
- *Texture.*—Medium.

Branches:
- *Form.*—Medium.
- *Texture.*—Smooth. Older wood—shaggy.
- *Color.*—Current season's growth: Dorsal side—Sherry Brown (15–E–12); ventral side—Fern Green (21–K–7). Older wood—variegated Olive Green (15–H–3), with longitudinal splitting of lighter color—dull India Buff (12–F–5).
- *Lenticels.*—Number—medium to few. Size—medium to large.

Leaves:
- *Size.*—Medium. Average length—3⅜" to 4¼". Average width—1⅝" to 1¾".
- *Form.*—Ovate to elliptical. Apex—acute to cuspidate. Base—acute to broadly acute. Leaf veins—pinnately net veined. Leaf buds—small; short; pointed.
- *Thickness.*—Medium.
- *Texture.*—Smooth and glabrous.
- *Color.*—Medium green. Dorsal side—Tartan Green (24–L–11). Ventral side—Cactus Green (22–G–7).
- *Margin.*—Glandular at tip of serrations; globose red glands; double crenate.
- *Petiole.*—Medium length; slender. Color: Dorsal—Spinach Green (22–J–7), with a slight reddish tinge; ventral—Verdant Green (20–K–5).
- *Glands.*—Average number—two (range—none to four). Usually alternate—some opposite. Medium; globose; green; positioned on petiole at base of blade.
- *Stipules.*—Average—two.

Flower buds:
- *Hardiness.*—Hardy.
- *Size.*—Medium to small.
- *Length.*—Medium to short.
- *Form.*—Plump; free.
- *Surface.*—Mostly glabrous.
- *Number.*—Numerous on spurs.
- *Color.*—White in popcorn stage.

Flowers:
- *Blooming period.*—Date of first bloom—Mar. 2, 1966. Date of full bloom—Mar. 8, 1966. Medium, as compared with other varieties. About seven to ten days after Burmosa (unpatented).
- *Size.*—Small—average 20 mm. when full open. Petals—average small. Pedicel averages 8–10 mm. in length.
- *Color.*—Waxy white.

Fruit:
- *Maturity when described.*—Eating hard—Oct. 11, 1965.
- *Date of first picking.*—About Oct. 4th.
- *Date of last picking.*—About Oct. 30th.
- *Size.*—Uniform; large to medium. Average diameter axially—1⅞" to 2⅛". Average transversely in suture plane—1⅞" to 2".
- *Form.*—Uniform; globose to slightly oblate.
- *Suture.*—An inconspicuous to distinct line; extends from cavity to apex tip.
- *Ventral surface.*—Rounded.
- *Lips.*—Equal; very inconspicuous.
- *Cavity.*—Flaring; rounded. Average depth—3/16". Average breadth—5/16". Markings none.
- *Base.*—Broadly rounded.
- *Apex.*—Rounded to truncate.
- *Fruit stem.*—Average diameter—1/16". Average length—½".

Skin:
- *Thickness.*—Thick.
- *Texture.*—Medium tough.
- *Tenacity.*—Tenacious to flesh.
- *Tendency to crack.*—None.
- *Color.*—Deep Purple-Blue (48–E–12), with a moderate to heavy Blue-Gray bloom (47–A–6). Light dots on skin.

Flesh:
- *Amygdalin.*—Moderate.
- *Juice.*—Moderate.
- *Texture.*—Firm; fine; crisp.

*Fibers.*—Inconspicuous; tender.
*Ripens.*—Evenly.
*Flavor.*—Subacid to mild.
*Aroma.*—Wanting.
*Eating quality.*—Good to very good.
*Color.*—Yellowish Amber (11–K–6). Surface of pit cavity—Yellowish Amber (11–K–6).

Stone:

*Type.*—Free to semifree; usually parts from flesh smoothly.
*Size.*—Small; plump. Average length—$1\frac{1}{16}''$. Average breadth—$\frac{5}{8}''$. Average thickness—$\frac{5}{16}''$.
*Form.*—Globose, with slight wing on ventral side.
*Base.*—Narrow; curved to oblique.
*Hilum.*—None evident.
*Apex.*—Rounded to acuminate.
*Sides.*—Equal.
*Surface.*—Irregularly furrowed near ventral edge toward apex.
*Ridges.*—Rounded from base to apex.
*Dorsal edge.*—Narrow, with shallow groove on either side, interrupted.
*Tendency to split.*—None.
*Kernel.*—Ovate; bitter; viable. Average length—$\frac{1}{2}''$. Average width—$\frac{3}{8}''$.

*Color.*—Medium Red (7–J–5).
Use: Market—local. Dessert; culinary.
Keeping quality: Good.
Resistance to insects: Good.
Shipping quality: Very good.

The plum tree and its fruit herein described may vary in slight detail due to climatic and soil conditions under which the variety may be grown; the present description being of the variety as grown in the Central Valley of California.

The following is claimed:

A new and distinct variety of plum tree, substantially as illustrated and described, which is a regular and productive bearer of fruit having yellowish amber flesh, a free to semi-free stone, and deep purple blue skin similar in color to that of the Queen Ann; the fruit being particularly characterized, as to novelty and in comparison to said Queen Ann, by a ripening period about four to five weeks later, and firmer flesh which does not soften as readily.

No references cited.

ABRAHAM G. STONE, *Primary Examiner.*
ROBERT E. BAGWILL, *Examiner.*